US006449333B1

United States Patent
Yamasaki

(10) Patent No.: US 6,449,333 B1
(45) Date of Patent: Sep. 10, 2002

(54) THREE-DIMENSIONAL FLUOROSCOPY AND X-RAY BULB FOR THE SAME

(76) Inventor: Tomoki Yamasaki, 5-1 Higashihangi-cho, Shimogamo, Sakyo-ku, Kyotu-shi, Kyoto 606-0824 (JP)

( * ) Notice: Subject to any disclaimer, the term of this patent is extended or adjusted under 35 U.S.C. 154(b) by 0 days.

(21) Appl. No.: 09/901,598

(22) Filed: Jul. 11, 2001

(30) Foreign Application Priority Data

Mar. 7, 2001 (JP) ........................................ 2001-063708

(51) Int. Cl.⁷ .............................................. G21K 4/00
(52) U.S. Cl. ........................................ 378/42; 378/41
(58) Field of Search ................... 378/42, 41, 98.12, 378/84

(56) References Cited

U.S. PATENT DOCUMENTS

| | | | | |
|---|---|---|---|---|
| 3,250,916 A | * | 5/1966 | Rogers | 378/41 |
| 5,073,914 A | * | 12/1991 | Asahina et al. | 378/42 |
| 6,167,111 A | * | 12/2000 | Watanabe et al. | 378/34 |

* cited by examiner

Primary Examiner—David P. Porta
Assistant Examiner—Elizabeth Gemmell
(74) Attorney, Agent, or Firm—Birch, Stewart, Kolasch & Birch, LLP

(57) ABSTRACT

An object of the present invention is to provide a three-dimensional fluoroscopy for continuous stereoscopic observation of a human blood vessel by using a contrast medium, 3-D visualization in nondestructive inspection of materials, baggage check and so on. The present invention also relates to an X-ray bulb for the three-dimensional fluoroscopy.

According to the three-dimensional fluoroscopy provided by the present invention, two X-ray beams are irradiated to an object from sources spaced from each other by an interpupillary distance of a human inspector, for projection of alternating X-ray images for the left eye and the right eye on a fluorescent screen for a predetermined exposure time and at a predetermined interval, and the images for the left eye and the images of the right eye are projected on a stereoscopic viewer continuously but independently from each other, thereby providing a three-dimensional fluoroscopic view.

1 Claim, 4 Drawing Sheets

Fig. 1

THREE-DIMENSIONAL FLUOROSCOPY AND X-RAY BULB FOR THE SAME

BACKGROUND OF THE INVENTION

The present invention relates to three-dimensional fluoroscopy for continuous stereoscopic observation of a human blood vessel by using a contrast medium, 3-D visualization in nondestructive inspection of materials, baggage check and so on. The present invention also relates to an X-ray bulb for the three-dimensional fluoroscopy.

To this date, fluoroscopy is only two-dimensional.

At present, there is no visual, continuous, three-dimensional fluoroscopy. Recently however, there is need in the field of engineering, medicine and so on for three-dimensional fluoroscopic imaging.

A difference between the present invention and the prior art fluoroscopy is in the number of X-rays (beams) radiated, namely, whether only one beam is used or two beams are used. Imaging with one beam of X-ray is equivalent to seeing an object with only one eye, whereas imaging with two X-ray beams is comparable to seeing the object with both eyes.

A conventional X-ray image only gives a two-dimensional view, but with two X-ray beams, the image gives a three-dimensional view. There are three methods for producing the three-dimensional view by using two X-ray beams.

A first method is to use two X-ray vacuum tubes (X-ray bulbs) simultaneously for generation of two X-ray beams, which are irradiated alternately to an object to obtain fluoroscopic images for stereoscopic viewing.

A second method is to use mirrors for making two X-ray beams from a single X-ray beam generated by one X-ray bulb.

A third method is to modify an X-ray bulb for generation of two X-ray beams.

In any of the methods described above, the two X-ray beams are spaced from each other by three to seven centimeters, because sources of the two X-ray beams should be spaced from each other as far as between the left and right pupils in a human. Experiments have established that the distance of five centimeters will give the most natural view.

EMBODIMENTS

Figure 1:
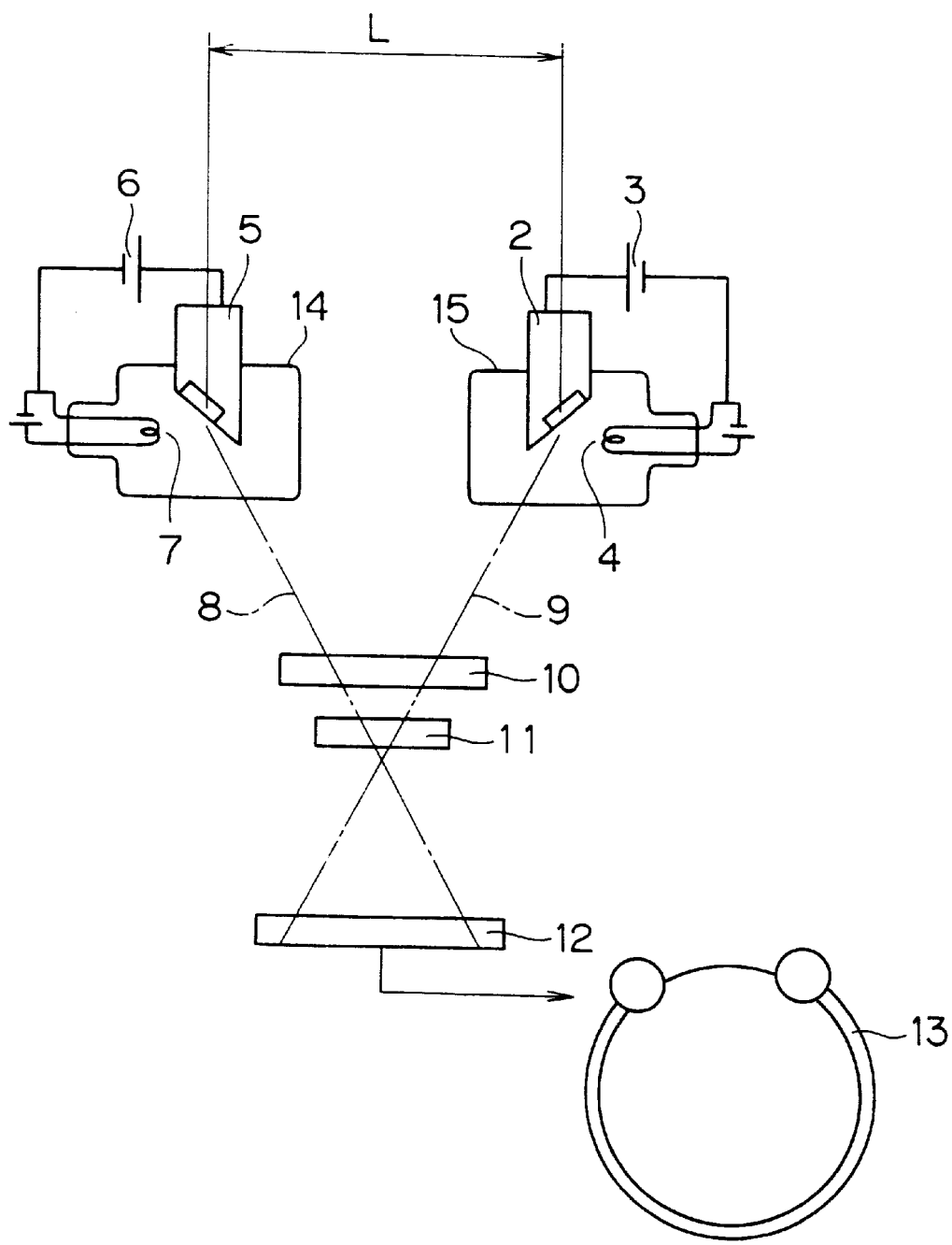
FIG. 1 is a diagram depicting a three-dimensional fluoroscopy for viewing an object stereoscopically from outside, by using two X-ray bulbs thereby generating two X-ray beams.

A first method uses two X-ray bulbs 14, 15, as shown in FIG. 1, for generation of two X-ray beams 8, 9. These two sources of the beams are spaced from each other by a distance L which is an interpupillary distance of a human inspector. Cathode rays come out of cathodes 7, 4 of respective X-ray bulbs 14, 15, hit on anodes 5, 2 and generates the left and the right X-ray beams 8, 9, which pass a shutter 10, penetrate an object 11 such as a blood vessel with a contrast medium injected therein according to the present embodiment, then reach and make a fluorescent screen 12 glow.

The shutter 10 opens and closes at a predetermined time interval, thereby alternately allowing the left and right X-ray beams to pass through, so as to project images alternately for the left and right eyes on the fluorescent screen 12. By using a stereoscopic viewer 13, the inspector can see a three-dimensional view of the object 11 such as the blood vessel, an organ and so on from outside of the body. This makes it possible to perform a treatment, a surgical operation and so on to an intertwined vessel for example, from outside of the body and under visual observation.

If applied to a nondestructive inspection, it becomes possible to give stereoscopic evaluation to an internal object from outside.

It should be noted here that components indicated by numeral codes 6, 3 are power sources for the anodes 5, 2 and cathodes 7, 4 respectively.

A second method uses one X-ray bulb 21. A cathode ray comes out of a cathode 25 to an anode 23, thereby generating an X-ray beam 27, which is then reflected by a rotating X-ray reflection mirror 29 made of a heavy metal alloy.

Figure 2:
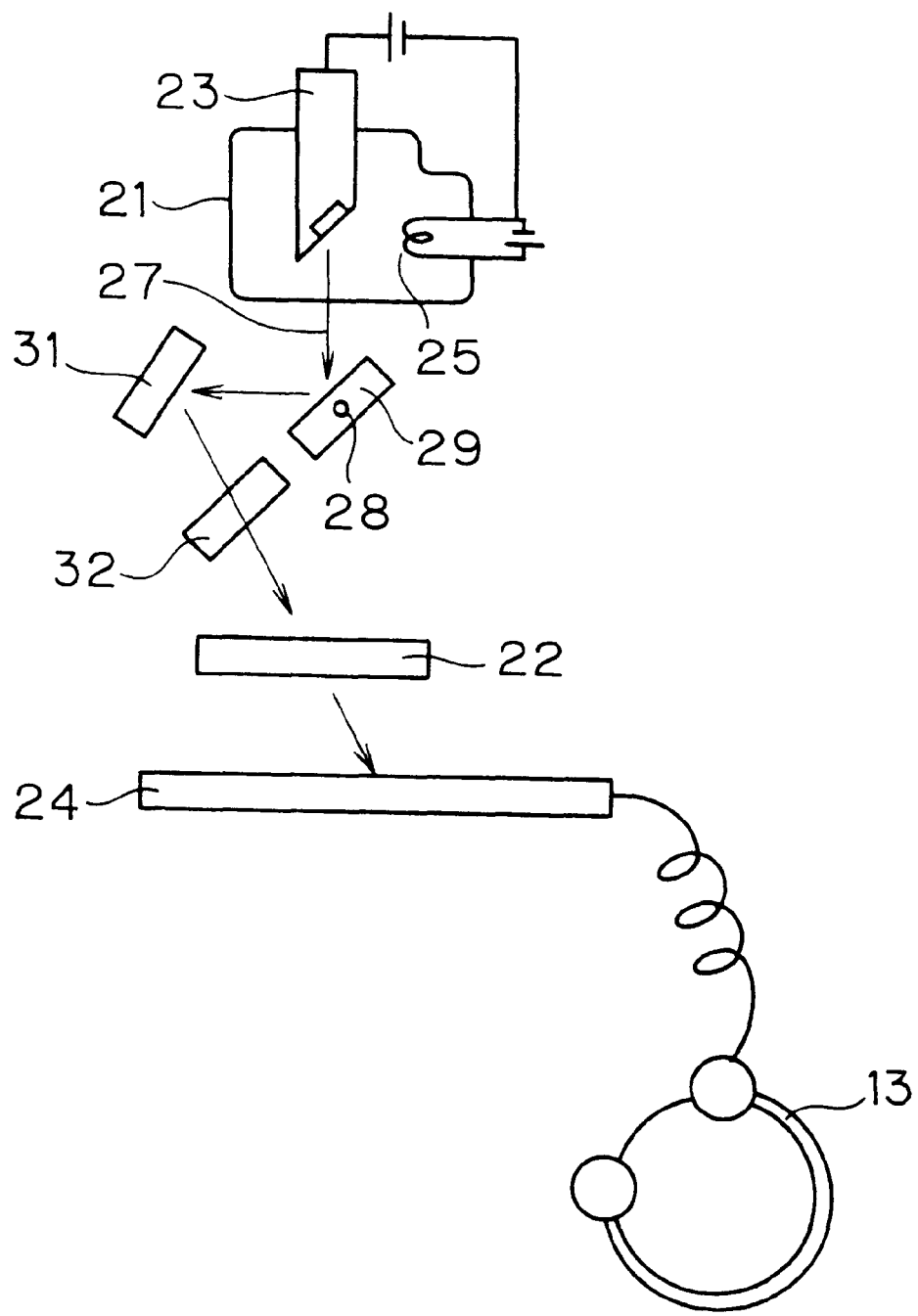
FIG. 2 is a diagram depicting a three-dimensional fluoroscopy for viewing an object stereoscopically from outside, by using an X-ray bulb thereby generating an X-ray beam, showing an arrangement for formation of a left-eye view.
Figure 3:
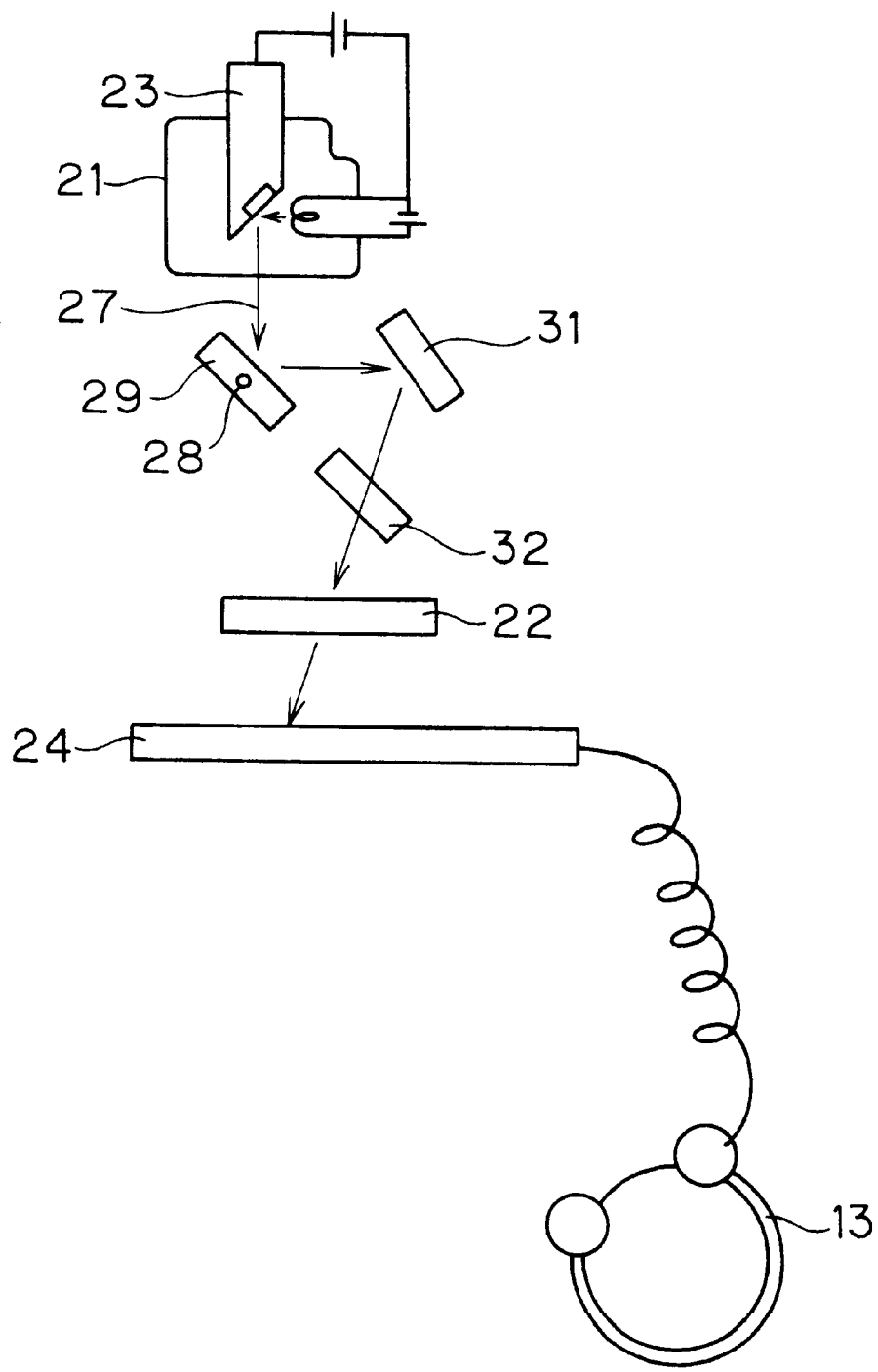
FIG. 3 is a diagram depicting a three-dimensional fluoroscopy for viewing an object stereoscopically from outside, by using an X-ray bulb thereby generating an X-ray beam, showing an arrangement for formation of a right-eye view.

By rotating a mirror-surface controlling shaft 28, the X-ray beam 27 is reflected in a left direction and a right direction as illustrated in FIG. 2 and FIG. 3 which respectively show an arrangement for formation of a left-eye view and an arrangement for formation of a right-eye view. This constitution, together with a set of reflector plates 31, provides two X-ray beams having an interpupillary distance of a human inspector and alternating at a predetermined time interval.

The above splitting of the X-ray beam for the left eye and the right eye also covers the function performed by the shutter 10 in FIG. 1. By the irradiation of these two X-ray beams to an object 22, images for each of the eyes are projected, independently a long time, on a fluorescent screen 24. By continuously viewing these images through a stereoscopic viewer 13, the object 22 can be observed three-dimensionally.

It should be noted here that the reflector plates 31 are movable, and so is the screen 32 as to allow focusing.

According to the second method, brightness of the obtained image may not be optimum, yet there is an economic and technical advantage that the 3-D image can be obtained with only one X-ray bulb.

Figure 4:
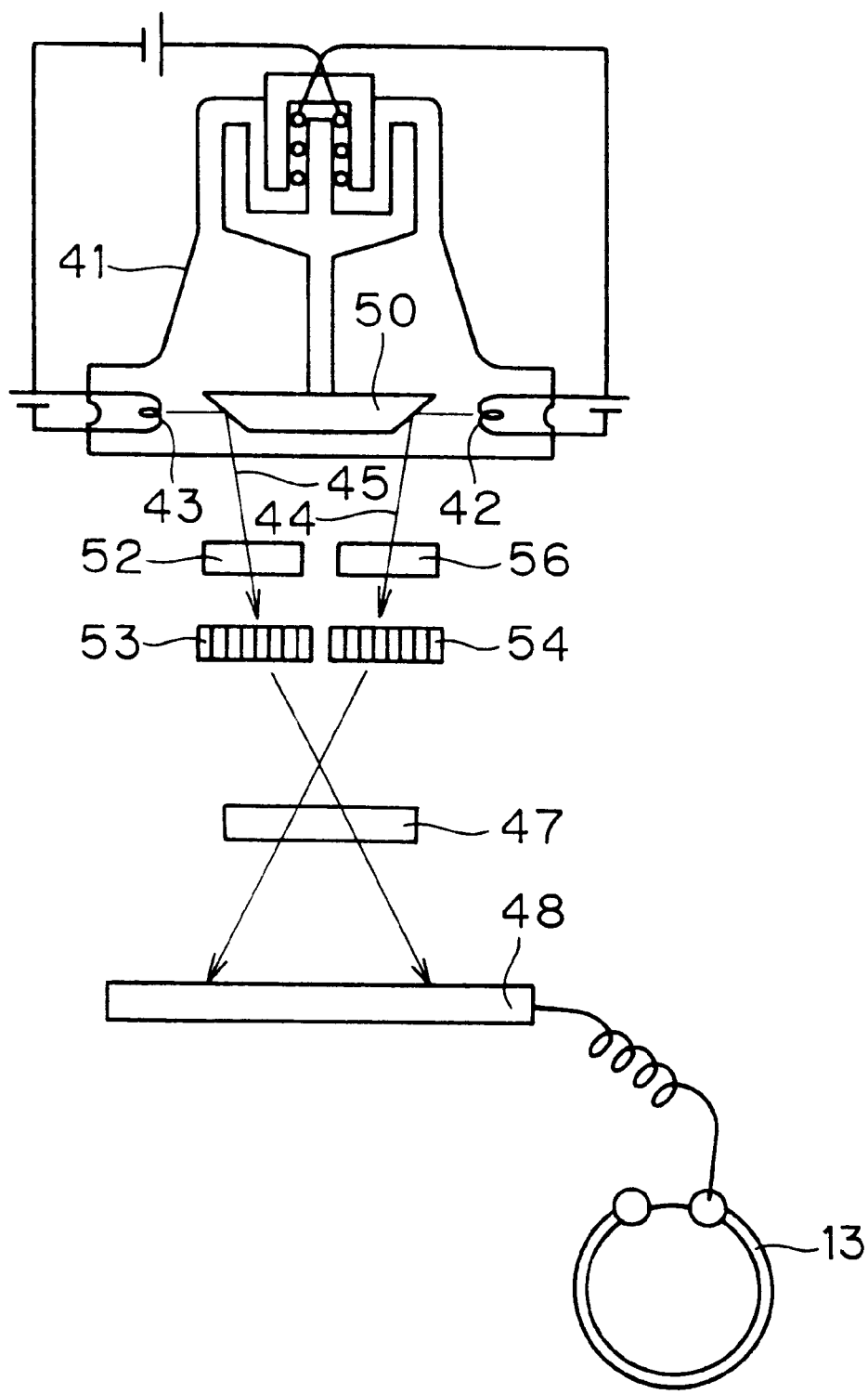
FIG. 4 is a diagram depicting a three-dimensional fluoroscopy for viewing an object stereoscopically from outside, by using an X-ray bulb thereby generating two X-ray beams.

A third method uses one X-ray bulb 41 as shown in FIG. 4. The X-ray bulb 41 generates two continuous X-ray beams 45, 44 coming out of sources spaced at an interpupillary distance.

This method uses a beveled, rotating, tungsten anode which is known publicly. In a known application, a cathode ray is generated in one direction, and an X-ray beam is produced in another direction from the anode plate. According to the present invention however, the cathode rays come in two directions, thereby generating corresponding X-ray beams in corresponding two directions from sources spaced at an interpupillary distance, and these two X-ray beams are utilized in the same way as in the first and the second methods for the three-dimensional fluoroscopy.

This method is described in more detail. Specifically, the X-ray bulb 41 has a center portion provided with a beveled, rotating anode 50, and a left and a right end portions provided with cathodes 43, 42 respectively.

The cathodes 43, 42 are heated to generate cathode rays hitting on the anode 50 at different angles, generating the X-ray beams 45, 44 coming at corresponding angles.

The X-ray beams pass respective shutters 52, 56 and filters 53, 54, and then penetrate an object 47 placed at a predetermined distance for a predetermined exposure time, projecting X-ray images on a fluorescent screen 48 in alternation for the left eye and the right eye.

By viewing these images through a stereoscopic viewer 13 independently but continuously with the left eye and the right eye, a three-dimensional fluoroscopic view can be observed. If this method is used in imaging a human body by using a contrast medium of various kinds, the obtained view can be utilized for a medical purpose. Further, the method can also be applied to various kinds of nondestructive inspection.

As has been described above, the present invention provides a three-dimensional fluoroscopy, wherein two X-ray beams are irradiated to an object from sources spaced from each other by an interpupillary distance of a human inspector, for projection of alternating X-ray images for the left eye and the right eye on a fluorescent screen for a predetermined exposure time and at a predetermined interval, and the images for the left eye and the images for the right eye are projected on a stereoscopic viewer continuously but independently from each other, whereby providing a three-dimensional fluoroscopic view. Therefore, it has become possible to perform continuous stereoscopic observation of a human blood vessel by using a contrast medium, 3-D visualization in nondestructive inspection of materials, baggage check and so on.

Further, the present invention provides a three-dimensional fluoroscopy, wherein one X-ray beam is reflected in a left direction and a right direction in alternation for a predetermined exposure time and at a predetermined interval by a rotating mirror, the reflected X-ray is further reflected by a pair of mirrors spaced from each other by an interpupillary distance of a human inspector, whereby irradiating two X-ray beams to an object in alternation. Therefore, it has become possible to perform continuous stereoscopic observation of a human blood vessel by using a contrast medium, 3-D visualization in nondestructive inspection of materials, baggage check and so on.

Further, the present invention provides a three-dimensional fluoroscopy, wherein one X-ray bulb has a beveled, rotating anode having a diameter generally equal to an interpupillary distance of a human, and two cathode rays are hit on the anode for generation of two X-ray beams from sources spaced at the interpupillary distance, whereby irradiating the two X-rays to an object in alternation for a predetermined exposure time and at a predetermined interval.

What is claimed is:

1. A three-dimensional fluoroscopy, wherein one X-ray beam is reflected in a left direction and a right direction in alternation for a predetermined exposure time and at a predetermined interval by a rotating mirror, the reflected X-ray beams being further reflected by a pair of mirrors spaced from each other by an interpupillary distance of a human inspector, whereby irradiating two X-ray beams to an object in alternation.

* * * * *